United States Patent [19]

Schoener et al.

[11] Patent Number: 5,514,592
[45] Date of Patent: May 7, 1996

[54] METHOD AND COMPOSITION FOR TESTING BLOOD FOR HEMOGLOBIN S THAT INCORPORATES MINERAL OIL AS AN INSOLUBLE UPPER PHASE

[75] Inventors: Dale Schoener, West Chester; Gwen Parkin, Oaks, both of Pa.

[73] Assignee: Medicus Technologies, Inc., West Chester, Pa.

[21] Appl. No.: 388,010

[22] Filed: Feb. 13, 1995

[51] Int. Cl.$^6$ ................................................ G01N 33/72
[52] U.S. Cl. ........................ 436/66; 436/8; 422/61; 435/2; 435/810
[58] Field of Search ........................ 436/8, 15, 63, 436/66, 174; 422/61; 435/2, 810

[56] References Cited

U.S. PATENT DOCUMENTS

| | | | |
|---|---|---|---|
| 3,492,095 | 1/1970 | Tillem | 436/66 |
| 3,607,695 | 9/1971 | Schneider | 204/182.7 |
| 3,761,226 | 9/1973 | Louderback et al. | 436/66 |
| 3,847,482 | 11/1974 | Sokol et al. | 356/40 |
| 3,847,545 | 11/1974 | Shanbrom et al. | 436/66 |
| 3,918,905 | 11/1975 | Warren et al. | 436/66 |
| 4,981,819 | 1/1991 | Rinn | 501/12 |

OTHER PUBLICATIONS

The Condensed Chemical Dictionary—10th edition, 1981, p. 1030.
Bowie et al. *Clinical Chemistry*, vol. 29, No. 2, 1983, pp. 325–328.
Warren et al. *American Journal of Medical Technology*, vol. 41, No. 9, Sep. 1975, pp. 317–321.

*Primary Examiner*—Robert J. Warden
*Assistant Examiner*—Maureen M. Wallenhorst
*Attorney, Agent, or Firm*—Caesar, Pivise, Bernstein et al.

[57] ABSTRACT

A method for testing blood for the presence of hemoglobin S wherein a blood sample is vigorously admixed with a two-phase test system for the purpose of determining the presence or absence of hemoglobin S after separation of the phases and wherein the two-phase test system involves an aqueous phase containing a lysing agent, a chemical reducing system and a phosphate ion buffer system; and an immiscible phase of mineral oil. The hemoglobin S presence is determinable by the color of a band formed at the interface of the aqueous and immiscible phases and wherein the invention further includes a composition suitable for testing whole blood for hemoglobin S.

8 Claims, No Drawings

METHOD AND COMPOSITION FOR TESTING BLOOD FOR HEMOGLOBIN S THAT INCORPORATES MINERAL OIL AS AN INSOLUBLE UPPER PHASE

BACKGROUND OF THE INVENTION

This invention is used in the laboratory determination of hemoglobin S, the abnormal hemoglobin which is responsible for Sickle Cell anemia. It is a solubility test. It is used along with electrophoresis or isoelectrofocusing procedures to make a definitive diagnosis for the presence of Hemoglobin S.

In U.S. Pat. No. 3,918,905 (Warren et al.), which is incorporated by reference herein, is disclosed a composition for determining the presence of sickling heterozygous or homozygous hemoglobin. That composition utilizes a two-phase composition comprising an aqueous phase containing a phosphate buffer system, a stable reducing agent system and a lysing agent. The aqueous phase is in combination with an organic phase, such as toluene, which is immiscible with the aqueous phase. By adding blood products to the claimed composition and performing the necessary steps of the analysis, one obtains a colorimetric determination of the genotype of the hemoglobin tested. For example, in that test, which produces various colored bands in the various immiscible phases, normal blood produces a middle band which is grey colored and the lower phase is red. A hemoglobin genotype of AS produces a middle band of dark red and a lower phase of pink. When the hemoglobin genotype is SS, the middle band is dark red and the lower phase is straw-colored or pale yellow.

While that method is capable of determining the hemoglobin genotype, it suffers from the deficiency of requiring an organic and toxic solvent such as toluene.

In the present invention, mineral oil has replaced the organic solvent such as toluene found in U.S. Pat. No. 3,918,905. Toluene, as the lighter immiscible phase, was the choice in 1975 because it had long been used as a lysing agent in hematology and as a preservative of biological fluids.

The aim of this invention is to eliminate the hazardous component toluene. Mineral oil is much safer. Mineral oil has a flash point of 177° C. Toluene has a flash point of 4° C. Mineral oil is not listed as hazardous by OSHA (Occupational Safety and Health Administration) or DOT (Department of Transportation). Also disposal problems are eliminated.

The results of the present invention are surprising and unexpected since the literature has reported that only toluene as the upper phase permits the accurate identification. In the American Journal of Medical Technology, Vol. 41, No. 9, September 1975, pages 317–321, Warren et al. reported on page 319, ¶13 that toluene as the upper phase appeared to be the most effective organic solvent of the several that were tried.

Accordingly, a need exists for a method and composition of determining hemoglobin genotype which does not utilize organic solvents.

OBJECTS OF THE INVENTION

Accordingly, it is a general object of this invention to provide a method and composition of determining hemoglobin genotype which overcomes the disadvantages of the prior art.

It is another object of this invention to provide a method, kit and composition of determining hemoglobin genotype which is reliable and safe and does not require the use of organic solvents.

It is a further object of this invention to provide a method, kit and composition of determining hemoglobin genotype which is reproducible.

SUMMARY OF THE INVENTION

These and other objects of this invention are achieved by providing a method for testing blood for the presence of hemoglobin S. The method comprises vigorously admixing a blood sample with a two-phase test system and determining the presence or absence of hemoglobin S after separation of the phases. The two-phase system comprises an aqueous phase containing a lysing agent, a chemical reducing system and a phosphate ion buffer system; and an immiscible phase consisting essentially of mineral oil. The hemoglobin S presence is determinable by the color of a band formed at the interface of the aqueous and immiscible phases. The invention further includes a kit and composition suitable for testing whole blood for hemoglobin S.

DETAILED DESCRIPTION OF THE PREFERRED EMBODIMENTS

The reagent is contained in a 12×75 mm glass vial. It consists of 2 mls (milliliters) of a high molarity phosphate buffer containing sodium bisulfite and saponin and 0.5 ml of an upper immiscible layer of mineral oil. Sodium bisulfite creates a low oxygen tension state. Saponin lyses the red blood cells. To perform the test, 100 microliters of whole blood is added to the vial which is then mixed well. Hemoglobins A, C, F, D are soluble in the lower aqueous phase. Hemoglobin S is relatively insoluble in the lower aqueous phase and a precipitate forms. After centrifugation, this insoluble hemoglobin forms a red band at the interface of the lower aqueous phase and the upper mineral oil phase. This test can distinguish between the heterozygous (AS, SC) and the homozygous (SS) condition.

Reagent preparation: To 920 ml of water, the following chemicals are added: 237 grams of potassium phosphate dibasic, 135 grams of potassium phosphate monobasic, 100 grams sodium bisulfite, and 10 grams sodium hydrosulfite. In a separate container, 10 grams of saponin is dissolved in 80 ml of water. The saponin solution is then added to the previously described solution and the entire mixture filtered down through at least a 1.2 um filter into a glass carboy. The final pH is 6.4±0.2. Two mls of this material is added to a 12×75 mm vial along with 0.5 ml of mineral oil and capped. The sodium hydrosulfite acts as a preservative by eliminating oxygen during the batch production and vialing operation. It decomposes in about 3 days. Sodium metabisulfite can replace sodium bisulfite. The reagent is stable for at least 1 year.

To perform the test, 100 microliters of fresh whole blood is added to the tube. It is then vortexed or shaken for 10 seconds. Then it is centrifuged at a minimum rcf of 1000 xg for 10 minutes. The tube is examined. There should be a clear lower aqueous phase, an upper immiscible mineral oil phase, and an interface of insoluble material between the two phases. If the lower phase is not clear, the tube is recentrifuged until it is clear. With patients having normal AA Hemoglobin, the lower aqueous phase is a deep red with a narrow gray interface. The hemoglobin A is soluble in the high molarity phosphate buffer, thus the reason for the red color. The narrow gray band is a combination red cell stroma and some other insoluble components. Since hemoglobin S is insoluble in the high molarity phosphate buffer, patients with SS hemoglobin show a lower aqueous phase that is yellow to amber with a red interface. Patients with heterozygous S (AS,SC) have a light red or pink lower aqueous phase with a red interface layer. The suggested sample is whole blood that is less than 10 days old and stored refrigerated during this time. For samples 10 days to 8 weeks old, add 18±2 mg of sodium hydrosulfite to reduce any methemoglobin that may have formed.

An alternate sampling procedure is to sample packed erythrocytes instead of whole blood. This procedure eliminates variations in color intensity due to varying hemoglobin levels. Whole blood is centrifuged at a minimum of 1000 xg for 10 minutes and the plasma removed. A 50 microliter positive displacement pipette is used to sample the packed erythrocytes and dispense them into the reagent tubes. It is then treated as described above. This sampling method is described in the publication titled Solubility test for confirming the presence of sickling hemoglobins, Approved Standard, National Committee for Clinical Laboratory Standards. NCCLS publication H10-A. Villanova, Pa. 1986.

CLINICAL TESTING

Eight one patients having unknown sickle cell anemia profiles were tested for sickle cell anemia utilizing the present invention. These individuals were tested simultaneously using Sicklequik and the R868 BHP Modified. A normal and abnormal sickle control was also tested with each run. The Sicklequik solution utilizes toluene as the upper phase. The R868 BHP Modified solution is the present invention utilizing mineral oil as the upper phase. The test results for both solutions were identical indicating that mineral oil is useful in the present invention.

Of the 81 patients tested, 66 were negative for HbS and 15 were positive for HbS. Seven of the positive patients were previously confirmed by hemoglobin electrophoresis to be positive for sickle cell anemia, however, the identity of these individuals was not disclosed at the time of testing using the present invention. The remaining 3 patients had tested positive with our current lot of Sicklequick.

|  | SICKLEQUIK | R868 BHP MODIFIED |
|---|---|---|
| RUN 1 |  |  |
| SPEC 1 | NEGATIVE | NEGATIVE |
| SPEC 2 | NEGATIVE | NEGATIVE |
| SPEC 3 | NEGATIVE | NEGATIVE |
| SPEC 4 | NEGATIVE | NEGATIVE |
| SPEC 5 | NEGATIVE | NEGATIVE |
| SPEC 6 | NEGATIVE | NEGATIVE |
| SPEC 7 | NEGATIVE | NEGATIVE |
| SPEC 8 | NEGATIVE | NEGATIVE |
| SPEC 9 | NEGATIVE | NEGATIVE |
| SPEC 10 | NEGATIVE | NEGATIVE |
| RUN 2 |  |  |
| SPEC 1 | POSITIVE | POSITIVE |
| SPEC 2 | POSITIVE | POSITIVE |
| SPEC 3 | NEGATIVE | NEGATIVE |
| SPEC 4 | NEGATIVE | NEGATIVE |
| SPEC 5 | NEGATIVE | NEGATIVE |
| SPEC 6 | NEGATIVE | NEGATIVE |
| SPEC 7 | NEGATIVE | NEGATIVE |
| SPEC 8 | NEGATIVE | NEGATIVE |
| RUN 3 |  |  |
| SPEC 1 | NEGATIVE | NEGATIVE |
| SPEC 2 | NEGATIVE | NEGATIVE |
| SPEC 3 | NEGATIVE | NEGATIVE |
| SPEC 4 | NEGATIVE | NEGATIVE |
| SPEC 5 | POSITIVE | POSITIVE |
| SPEC 6 | POSITIVE | POSITIVE |
| SPEC 7 | POSITIVE | POSITIVE |
| SPEC 8 | NEGATIVE | NEGATIVE |
| RUN 4 |  |  |
| SPEC 1 | NEGATIVE | NEGATIVE |
| SPEC 2 | NEGATIVE | NEGATIVE |
| SPEC 3 | NEGATIVE | NEGATIVE |
| SPEC 4 | NEGATIVE | NEGATIVE |
| SPEC 5 | NEGATIVE | NEGATIVE |
| SPEC 6 | NEGATIVE | NEGATIVE |
| SPEC 7 | NEGATIVE | NEGATIVE |
| RUN 5 |  |  |
| SPEC 1 | NEGATIVE | NEGATIVE |
| SPEC 2 | POSITIVE | POSITIVE |
| SPEC 3 | POSITIVE | POSITIVE |
| SPEC 4 | NEGATIVE | NEGATIVE |
| SPEC 5 | NEGATIVE | NEGATIVE |
| SPEC 6 | NEGATIVE | NEGATIVE |
| SPEC 7 | POSITIVE | POSITIVE |
| SPEC 8 | POSITIVE | POSITIVE |
| SPEC 9 | POSITIVE | POSITIVE |
| SPEC 10 | NEGATIVE | NEGATIVE |
| RUN 6 |  |  |
| SPEC 1 | POSITIVE | POSITIVE |
| SPEC 2 | POSITIVE | POSITIVE |
| SPEC 3 | POSITIVE | POSITIVE |
| SPEC 4 | NEGATIVE | NEGATIVE |
| SPEC 5 | NEGATIVE | NEGATIVE |
| SPEC 6 | POSITIVE | POSITIVE |
| SPEC 7 | POSITIVE | POSITIVE |
| RUN 7 |  |  |
| SPEC 1 | NEGATIVE | NEGATIVE |
| SPEC 2 | NEGATIVE | NEGATIVE |
| SPEC 3 | NEGATIVE | NEGATIVE |
| SPEC 4 | NEGATIVE | NEGATIVE |
| SPEC 5 | NEGATIVE | NEGATIVE |
| SPEC 6 | NEGATIVE | NEGATIVE |
| SPEC 7 | NEGATIVE | NEGATIVE |
| SPEC 8 | NEGATIVE | NEGATIVE |
| SPEC 9 | NEGATIVE | NEGATIVE |
| RUN 8 |  |  |
| SPEC 1 | NEGATIVE | NEGATIVE |
| SPEC 2 | NEGATIVE | NEGATIVE |
| SPEC 3 | NEGATIVE | NEGATIVE |
| SPEC 4 | NEGATIVE | NEGATIVE |
| SPEC 5 | NEGATIVE | NEGATIVE |
| SPEC 6 | NEGATIVE | NEGATIVE |
| RUN 9 |  |  |
| SPEC 1 | NEGATIVE | NEGATIVE |
| SPEC 2 | NEGATIVE | NEGATIVE |
| SPEC 3 | NEGATIVE | NEGATIVE |
| SPEC 4 | NEGATIVE | NEGATIVE |
| SPEC 5 | NEGATIVE | NEGATIVE |
| SPEC 6 | NEGATIVE | NEGATIVE |
| SPEC 7 | NEGATIVE | NEGATIVE |
| SPEC 8 | NEGATIVE | NEGATIVE |
| SPEC 9 | NEGATIVE | NEGATIVE |
| RUN 10 |  |  |
| SPEC 1 | NEGATIVE | NEGATIVE |
| SPEC 2 | NEGATIVE | NEGATIVE |
| SPEC 3 | NEGATIVE | NEGATIVE |
| SPEC 4 | NEGATIVE | NEGATIVE |
| SPEC 5 | NEGATIVE | NEGATIVE |
| SPEC 6 | NEGATIVE | NEGATIVE |
| SPEC 7 | NEGATIVE | NEGATIVE |

In addition, data was also generated utilizing the present invention, in a blind study on 99 total patients, 59 of whom were normal and 40 of whom were heterozygous S. The blood of each of these patients was also tested by hemoglobin electrophoresis to determine the hemoglobin composition. The present invention reached identical results on sickle cell composition for all 99 patients without any error.

Without further elaboration the foregoing will so fully illustrate our invention that others may, by applying current or future knowledge, adapt the same for use under various conditions of service.

We claim:

1. A method for testing blood for the presence of hemoglobin S comprising vigorously admixing a blood sample with a two-phase test system and determining the presence or absence of hemoglobin S after separation of the phases, the two-phase system comprising:
   (a) an aqueous phase containing a lysing agent, a chemical reducing system and a phosphate ion buffer system; and
   (b) an immiscible phase consisting essentially of mineral oil; the hemoglobin S presence being determinable by the color of a band formed at the interface of the aqueous and immiscible phases.

2. The method of claim 1 wherein the color of the aqueous phase enables differentiation between a heterozygous S and homozygous S condition of the blood sample.

3. The method of claim 1 wherein the lysing agent comprises saponin.

4. The method of claim 1 wherein the chemical reducing system comprises sodium bisulfite and sodium hydrosulfite.

5. A composition suitable for testing whole blood for hemoglobin S comprising:
   (a) an aqueous phase containing a lysing agent, a chemical reducing system and a phospate ion buffer system; and
   (b) an immiscible phase consisting essentially of mineral oil.

6. The composition of claim 5 wherein the lysing agent is saponin.

7. The composition of claim 5 wherein the chemical reducing system is composed of sodium bisulfite and sodium hydrosulfite.

8. A kit suitable for testing whole blood for hemoglobin S comprising:
   (a) an aqueous phase containing a lysing agent, a chemical reducing system and a phosphate ion buffer system; and
   (b) an immiscible phase consisting essentially of mineral oil.

* * * * *